(12) United States Patent
Krivoi et al.

(10) Patent No.: US 6,727,695 B2
(45) Date of Patent: Apr. 27, 2004

(54) TEST METHOD AND APPARATUS FOR NONCONTACT AND NONDESTRUCTIVE RECOGNITION OF IRREGULARITIES IN THE WALL THICKNESS OF FERROMAGNETIC PIPES

(75) Inventors: Guennadi Krivoi, Berlin (DE); Johannes Peter Kallmeyer, Holle OT Sillium (DE)

(73) Assignee: NP Inspection Services GmbH, Hildesheim (DE)

( * ) Notice: Subject to any disclaimer, the term of this patent is extended or adjusted under 35 U.S.C. 154(b) by 0 days.

(21) Appl. No.: 10/269,007

(22) Filed: Oct. 9, 2002

(65) Prior Publication Data
US 2003/0201771 A1 Oct. 30, 2003

(30) Foreign Application Priority Data

Apr. 24, 2002 (EP) .............................. 02009151

(51) Int. Cl.[7] .................. G01N 27/26; G01N 27/72; G01N 27/82; G01R 33/02; G01B 7/06
(52) U.S. Cl. ................ 324/263; 324/229; 324/71.2; 204/404
(58) Field of Search ........................ 204/404

(56) References Cited

U.S. PATENT DOCUMENTS 4,048,558 A * 9/1977 Goodman
5,126,654 A * 6/1992 Murphy et al. ............ 324/71.2
6,239,593 B1 * 5/2001 Burkhardt et al. ...... 324/220 X
6,281,697 B1 * 8/2001 Masuda et al. ......... 324/263 X
6,501,266 B1 * 12/2002 Krivoi et al. ........... 324/263 X

FOREIGN PATENT DOCUMENTS

DE   19819066   * 11/1999

* cited by examiner

*Primary Examiner*—Gerard R. Strecker
(74) *Attorney, Agent, or Firm*—J.C. Patents

(57) ABSTRACT

An electric current comprising a plurality of harmonic components is passed through the pipe under test, a magnetic field produced by it outside the pipe is measured, a spectrum of the electric current is measured, a spectrum from measured magnetic field data is also obtained. The ratios between identical spectral components of the current and magnetic field are evaluated. The test apparatus comprises a current source supplying an electric current, a means for measuring and storing momentary current values, a means for evaluating a current spectrum to define harmonic components of the electric current, at least one magnetic field sensor for measuring and storing momentary values of the magnetic field produced outside the pipe by the current, a means for evaluating the magnetic field spectrum to define harmonic components of the magnetic field, and a means for comparing and analyzing the obtained spectral data of the current and magnetic field.

2 Claims, 5 Drawing Sheets

TEST METHOD AND APPARATUS FOR NONCONTACT AND NONDESTRUCTIVE RECOGNITION OF IRREGULARITIES IN THE WALL THICKNESS OF FERROMAGNETIC PIPES

CROSS-REFERENCE TO RELATED APPLICATION

This application claims the priority benefit of European application serial no. 02009151.8, filed Apr. 24, 2002.

BACKGROUND OF THE INVENTION

1. Field of the Invention

The present invention relates to a method of testing for the recognition of irregularities in the wall thickness of ferromagnetic pipes as well as the test apparatus especially designed for the implementation of the test method.

2. Description of the Related Art

In the oil and gas industry, mainly steel pipes are used to transport the product. Normally these are made from fern tic steel, which show distinct ferromagnetic characteristics. Corrosion, or wall thickness reduction, in the pipes is caused by the influence from external as well as internal factors. This may lead to product loss and, as a result, to environmental damage. As a preventive measure, the pipes are periodically tested so that wall thickness changes can be detected in time. Nowadays, the following methods are used to test these pipes: (i) the so-called intelligent pig and (ii) the so-called NoPig Method. Intelligent Pigs are, for example, described in the "Non-destructive Testing Handbook, 2$^{nd}$ Ed., Vol. 10, Non-destructive Testing Overview, American Society for Non-destructive Testing, 1996, S. 252". An intelligent pig can be equipped with various sensors, utilizing ultrasound or magnetic flux leakage, to measure the actual wall thickness along the pipeline. The pig is inserted into the pipeline to be inspected and is transported through the line by the movement of the product flowing through the pipe. The measurement data are stored in the memory banks within the pig and will be evaluated once the pig has been removed from the line.

The disadvantage of the intelligent pig is the strict standards in which the pipelines must be built to accommodate the pig: for example, special channels must be available to insert and retrieve the pig, sharp bends, dents, different pipe diameters used in one pipeline are not allowed etc. The areas in which the pig can be efficiently used are therefore significantly reduced to the pipelines that have been specifically designed for this inspection method.

The U.S. Pat. No. 4,048,558 refers to a method in which a current will be passed through a metal pipe at different frequencies and its impedance is monitored. Should a change in the wall thickness occur, then the impedance should change as well. The disadvantage of this method is the minimal sensitivity and the problem that the defects can not be precisely located.

The German Patent Application DE 19819066 A1 refers to a non-contact inspection method for the recognition of wall thickness irregularities in inaccessible metal pipes. This method uses electric currents of different frequencies that flow through the pipe wall and induce magnetic fields that can be measured outside of the pipe. Through varying magnetic field penetration depths in the pipeline at lower and higher frequencies, the magnetic fields at these frequencies outside of the pipe will also vary when a defect is present of the pipe. This is caused by the deviation of the cross-sectional form of the pipe from the ring at the defect location. The current distribution in the cross section of the pipe will differ by varying frequencies so that the current weight center does not necessarily lie on the pipe symmetry axis. This causes the corresponding changes to the magnetic fields outside of the pipe. Above a pipe section containing no defects, the magnetic fields outside the pipe generated by varying frequencies will remain equal because the current centers will remain on the symmetrical axis of the pipe even by different frequencies. Defects will be found by comparing the measured magnetic field data at varying frequencies. It is necessary to sequentially scan the magnetic field along the pipe. This method is known as the NoPig Method (see http://www.finoag.com). This method does not have the disadvantage that pigs do in that no special preparation of the pipe is necessary and does not have to have the extra facilities to allow for the inserting of the inspection tool.

Nevertheless, the NoPig Method does have shortcomings. In the case of steel pipes, which tend to be made from ferritic steel, it is not satisfactory to measure the magnetic fields induced by two currents (one of them at a low frequency, and the other one with a higher frequency) and then to compare. Due to a rather high magnetic permeability of steel, the magnetic field in the pipe wall is much stronger than outside the pipe. In the case of a defect a stray magnetic flux arises from the defect area. As this takes place, the following describes the magnetic field outside the pipe: the stray magnetic flux acts against the displacement of the weight center of the current distribution. In the extreme case the magnetic field values to be measured are identical at low and high frequencies despite of an available defect. This compensating interaction of both mechanisms mentioned above depends on causes such as magnetic permeability and electrical conductivity of the steel used, and the geometric shape of a defect. This results in an essential reduction of the method and even in a full non-sensitivity to some defects.

SUMMARY OF THE INVENTION

In the light of the foregoing, it is an object of the present invention to provide a method and an apparatus for the recognition of irregularities in the wall thickness of ferromagnetic pipes, which makes it possible to, non-destructively and non-contacting, detect and to define places with reduced wall thickness on a pipe, despite of the fact that the pipe is made of a ferritic steel.

In accordance to the above objects and other advantages of the present invention, a non-destructive test method and a corresponding test apparatus for non-contacting recognition of irregularities in the wall thickness of ferromagnetic pipes are provided. Such irregularities are caused mainly by corrosion. For this reason the invention is especially intended for preventive recognition of corrosion caused wall thickness losses in oil and gas pipelines because they are made mainly from ferritic steel. The test method implies that an electric current consisting of many harmonic components is passed through the pipe tinder test and the magnetic field produced by the current will be measured. Therewith the frequency spectrum of the current is measured. The frequency spectrum of the measured magnetic field values is also calculated. The ratio between identical spectral components of the current and that of the magnetic field is calculated and used for the defect evaluation. The frequency range of the harmonic components is chosen in such a way, that the lowest frequency corresponds to the skin effect depth, which is at least as large as the nominal wall thickness of the pipe under test. The highest frequency corresponds to the skin effect depth which is at least as small as the critical residual wall thickness of the pipe under test. The critical residual wall thickness means the minimum allowed residual wall thickness on corroded areas. Since the ratio of the magnetic field outside the pipe at the place of corrosion to the current is frequency-dependent, this frequency dependence will be found from a comparison of spectral values of the magnetic field and of the current. In this way a defect will be recognized. In the case of a pipe section without any defects the ratio of the magnetic field outside the pipe to the current is frequency-independent. The test apparatus consists of two parts: a stationary current source and a mobile unit intended for magnetic field measurements. Both elements are transportable.

DETAIL DESCRIPTION OF THE EMBODIMENTS

Other properties, merits and possibilities for use of the actual invention will be evident in the following description of the preferred realization examples illustrated by figures.

Figure 1A:
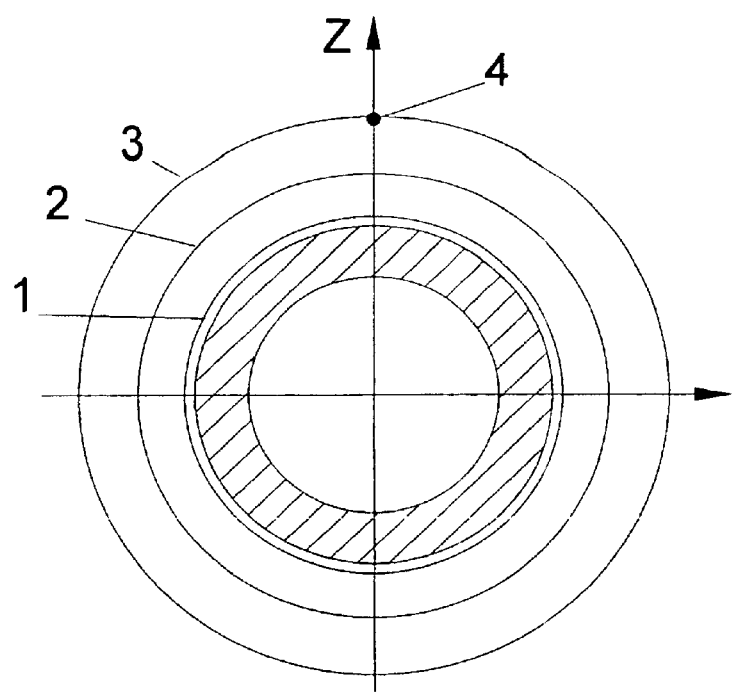
FIG. 1a shows a cross-section of a pipe without any defects and magnetic field lines in the case if an electric alternating current is passed through the pipe.
Figure 1B:
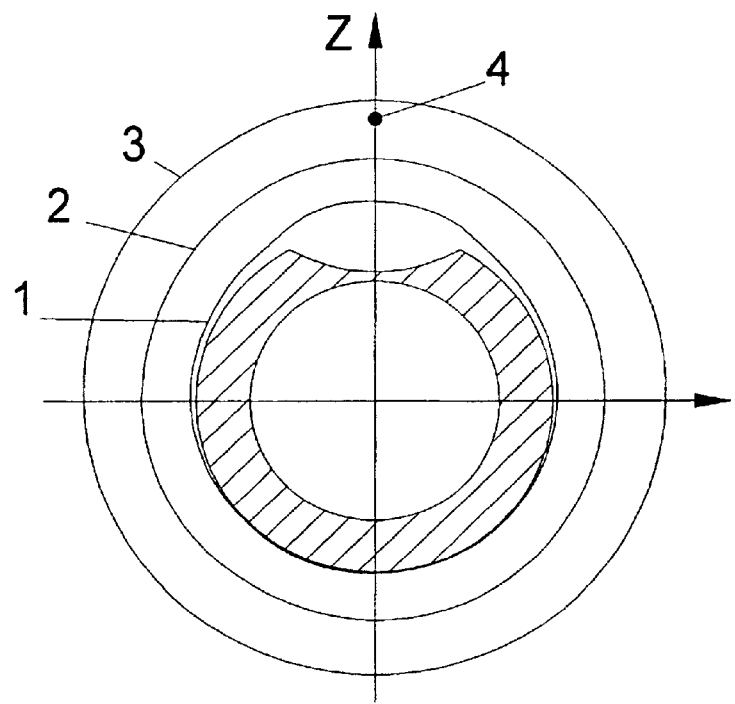
FIG. 1b shows a cross-section of a pipe with a defect and magnetic field lines if the same electric current is passed through the pipe.

FIG. 1a shows a cross-section of a pipe without any defects and magnetic field lines in the case if an electric alternating current is passed through the pipe. The current has a frequency lying in the frequency range used for measurements. The shown magnetic field lines represent the amplitude values of the A.C. magnetic field. FIG. 1b shows a cross-section of a pipe with a defect and magnetic field lines if the same electric current is passed through the pipe.

Figure 2:
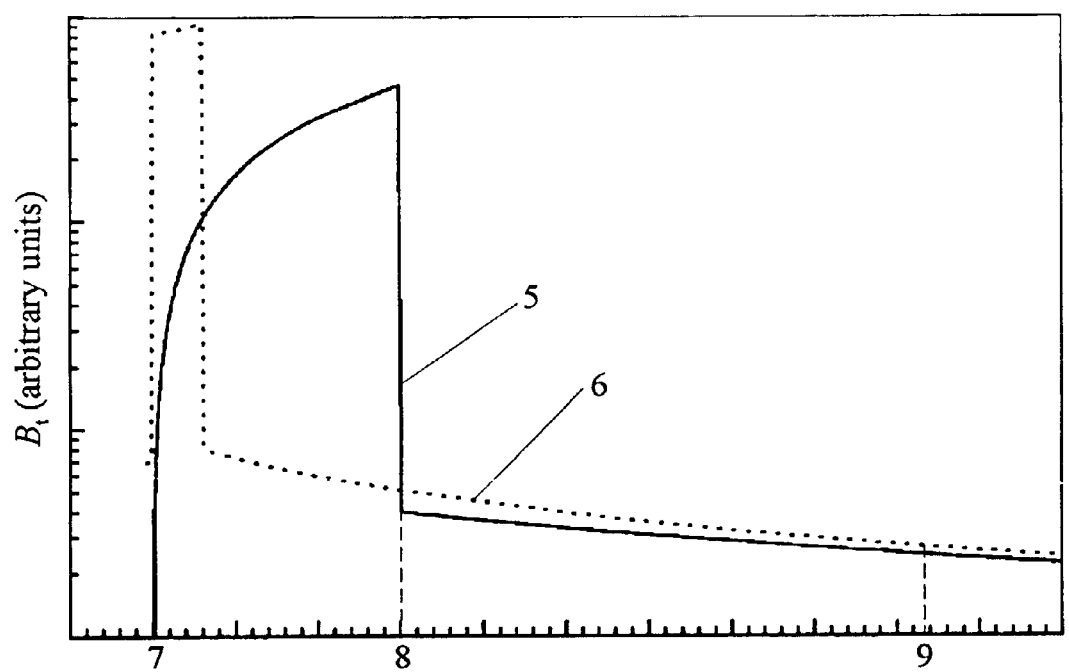
FIG. 2 shows the variation of the tangential component of the magnetic field along the axis Z in two cases shown in FIG. 1.

FIG. 2 shows the variation of the tangential component of the magnetic field along the axis Z in two cases shown in FIG. 1: (i) with no defect and (ii) with a defect. The vertical axis is plotted in the logarithmic scaling.

Figure 3:
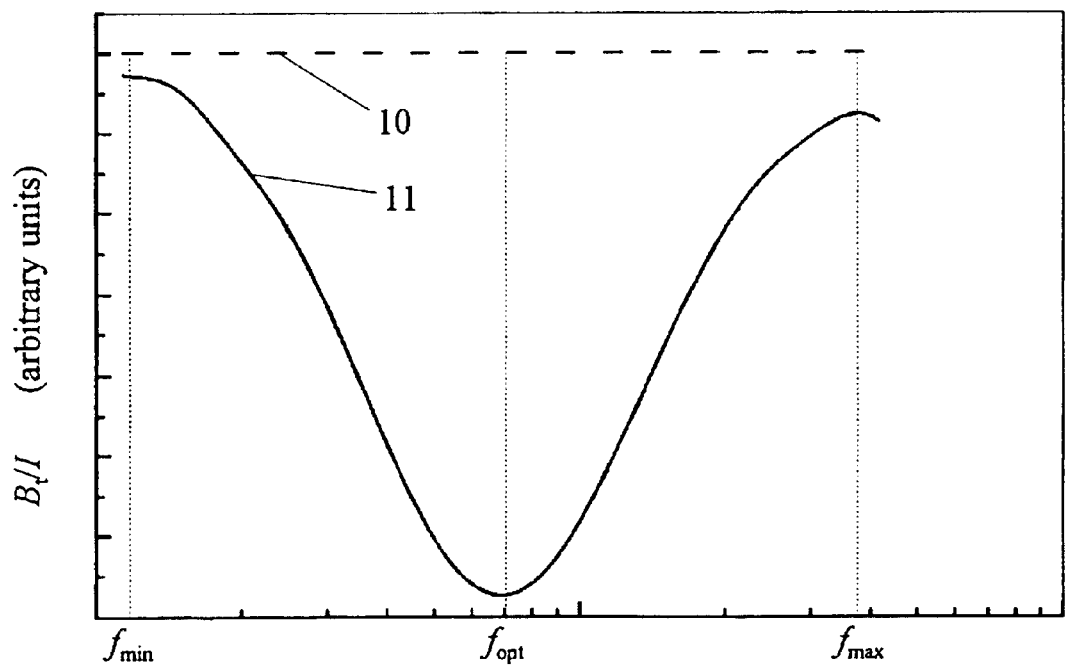
FIG. 3 shows the frequency dependence of the ratio between the tangential component of the magnetic field amplitude outside the pipe and the amplitude of the current passed through the pipe in both cases shown in FIG. 1.

FIG. 3 shows the frequency dependence of the ratio between the tangential component of the magnetic field amplitude outside the pipe and the amplitude of the current passed through the pipe in both cases shown in FIG. 1 (without and with a defect).

Figure 4:
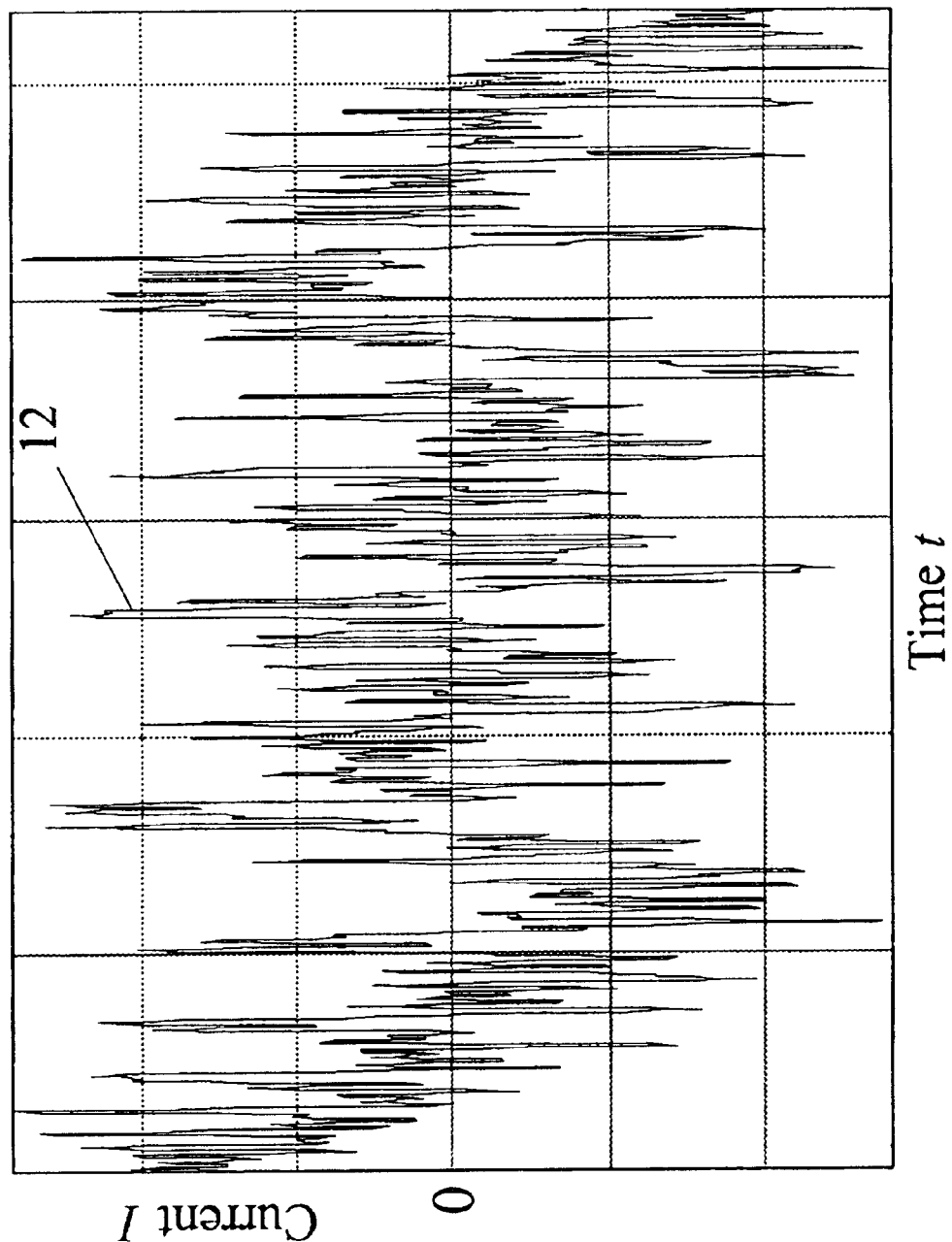
FIG. 4 shows as example the time dependence of the current passed through the pipe according to the present invention.

FIG. 4 shows as example the time dependence of the current passed through the pipe.

Figure 5:
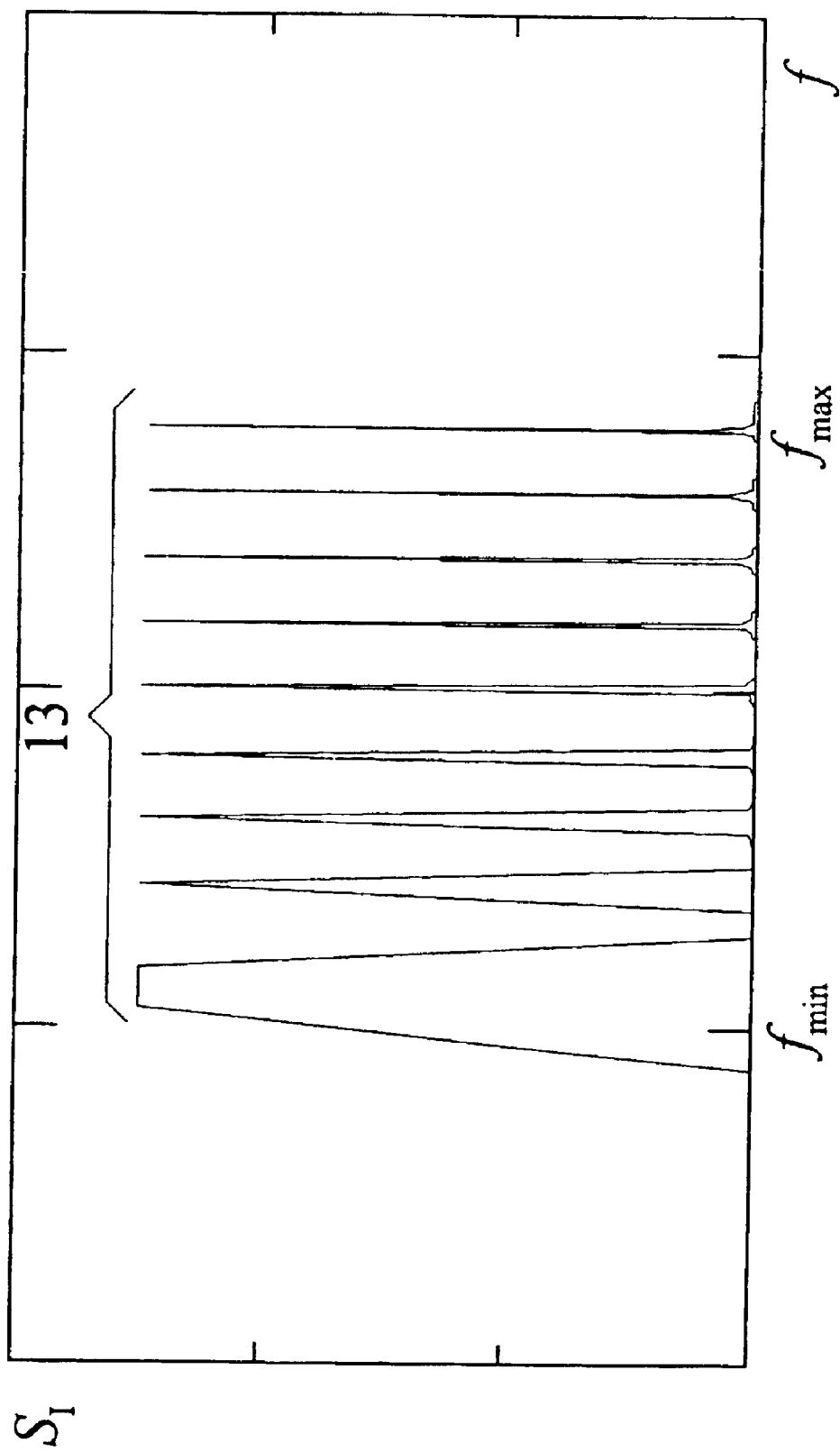
FIG. 5 shows as example the spectrum of the current passed through the pipe according to the present invention.

FIG. 5 shows as example the spectrum of the current passed through the pipe.

Figure 6:
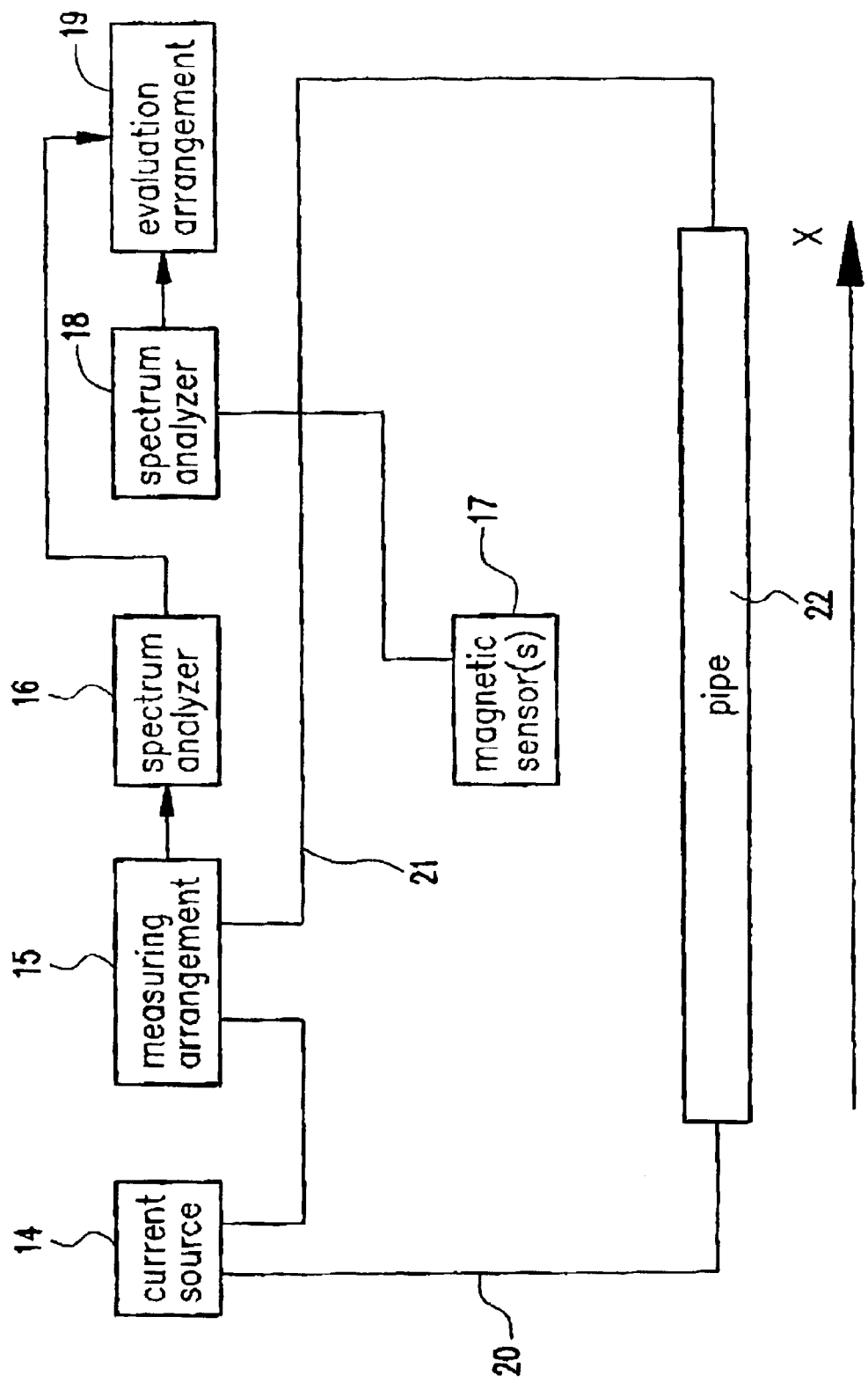
FIG. 6 shows a block diagram of the test apparatus intended for utilizing the test method of the present invention.

FIG. 6 shows a block diagram of the test apparatus intended for utilizing this test method.

During testing, an electric alternating current consisting of many harmonic components is passed through the pipe under test. The current flows in the pipe's axial direction in the pipe wall. In FIG. 1 pipe cross-sections in two different cases are shown. Additionally in the FIGS. 1a and 1b, the magnetic field lines are shown which represent the amplitude values of the A.C. magnetic field numerically calculated. FIG. 1a shows the case with no defect for one of harmonic components of the alternating current. FIG. 1b shows the case with a defect for the same harmonic component. In the case with no defect the magnetic field lines are round and concentric (see FIG. 1a) and independent of frequency. In the case of a defect, the magnetic field lines have a significant deviation from the round and concentric shape. This deviation is dependent on the defect geometry, on physical properties of the pipe material like magnetic permeability $\mu$ and electrical conductivity $\sigma$, and on the frequency $f$ of the harmonic current components. Therewith two different physical mechanisms are responsible for this frequency-dependent magnetic field deformation: the skin-effect and the stray magnetic flux. The skin-effect takes place in all leading media where an alternating current is flowing. In the case of a pipe carrying an alternating current the skin-effect is responsible for the radial distribution of the current density in the pipe wall. At higher frequencies the alternating current is forced out towards the outer surface of the pipe. A characteristic parameter used for definition of the skin-effect is the skin depth $\delta$ which describes the depth from the outer surface in a leading material where the alternating current density decreases in e=2.72 times compared to the density on the surface:

$$\delta = 2/2\mu\mu_o\sigma\omega)^{1/2}. \qquad (1)$$

Here $\mu_o$ is the magnetic permeability of vacuum, and $\omega=2\pi f$ is the angular frequency. The stray magnetic flux takes place where a regular edge-free geometrical shape is changed and thus magnetic resistance is increased. In the case of a pipe region containing a defect the shape of the cross-section is not more round than it was initially, and the magnetic flux comes out there which results in a deformation of the initially round and concentric magnetic field. Both mechanisms described above are valid for a defect region and can act compensating each other. The magnetic field lines 1 shown in FIGS. 1a and 1b are drawn for same values in both cases (without and with a defect). The same is valid for the magnetic field lines 2 and 3. The magnetic flux density B for these lines has following interrelation:

$$B_1 > B_2 > B_3. \qquad (2)$$

The indices mean the numbers of the magnetic field lines. In a measuring point 4 outside the pipe, e.g., the tangential component $B_t$ of the magnetic field is measured. For the example shown in FIG. 1b where a defect case is presented, the magnetic field measured in the point 4 is higher than in FIG. 1a where no defect is present. The plots in FIG. 2 illustrate this. The logarithmic scale is used for the axis $B_t$.

The variation of the tangential component $B_t$ of the magnetic field in the pipe wall and outside it along the axis Z used in FIG. 1 is shown in FIG. 2 as result of a numeric field modeling at some current frequency. The curve 5 corresponds to the case with no defect, and the curve 6—to the case with a defect. The points 7 and 8 on the axis Z correspond to the inner and outer pipe radius, respectively. The point 9 corresponds to the measuring point 4 in FIG. 1.

The magnetic field values of curves 5 and 6 at the point 9 are distinctly different. Using this, one can recognize a defect region.

The magnetic field depends directly on the current. For this reason a ratio between field and current values is used for the evaluation of measured data. A numerically calculated example of the frequency dependence of the ratio between the tangential component $B_t$ of the magnetic field outside the pipe and the current I flowing in the pipe wall is shown in FIG. 3 for both cases presented in FIG. 1 (without and with a defect). The frequencies $f_{min}$ and $f_{max}$ are the minimum and maximum values of the frequency range of the harmonic current components. The line 10 corresponds to the case with no defect, and the curve 11—to the case with a defect. As seen in FIG. 3, despite of the fact that the ratio to be evaluated is rather identical at frequencies $f_{min}$ and $f_{max}$ in both cases, at least one optimum frequency $f_{opt}$ exists, at which a significant difference between the cases without and with a defect is given. If the current passed through the pipe contains many harmonic components which frequencies are distributed in the range from $f_{min}$ to $f_{max}$, the whole frequency response of the ratio $B_t/I$ can be determined during one measurement and than evaluated to recognize defects. The character of the frequency response is caused by defect kind. Using this concept, different defects can be recognized.

An example of the time dependence of the test current I containing many frequency components is shown in FIG. 4. The current curve 12 is presented here as momentary current values against the time t. The frequency spectrum $S_I$ of this test current is shown in FIG. 5. It consists of many spectral lines 13 corresponding the harmonic components in the frequency range from $f_{min}$ to $f_{max}$.

FIG. 6 shows the block diagram of the test apparatus connected to a pipe to be tested. It consists of the current source 14, the arrangement 15 to measure the test current, the spectrum analyzer 16 of measured current data, magnetic field sensor or sensors 17, the spectrum analyzer 18 of measured magnetic field data, and the evaluation arrangement 19. To the output contacts 20 and 21 of the test apparatus is connected the pipeline under test. During testing the magnetic field sensor or sensors will be moved along the pipe in the X direction and the magnetic field will be measured and the obtained data will be stored. Simultaneously the test current will be measured and the obtained data will be also stored. After a spectral analysis of both data groups the ratio $B_t/I$ for each harmonic component will be calculated and analyzed. If the frequency response of the ratio $B_t/I$ is flat, there is no defect in the pipe. Otherwise, in the case of a non-flat frequency response with extrema it deals with a defect region in the pipe. A more detailed analysis of found defects is possible using the character of the frequency response.

While the invention has been described in conjunction with a specific best mode, it is to be understood that many alternatives, modifications, and variations will be apparent to those skilled in the art in light of the a foregoing description. Accordingly, it is intended to embrace all such alternatives, modifications, and variations which fall within the spirit and scope of the included claims. All matters set forth herein or shown in the accompanying drawings are to be interpreted in an illustrative and non-limiting sense.

What is claimed is:

1. A test method for noncontact and nondestructive recognition of irregularities in the wall thickness of ferromagnetic pipes, comprising:

passing an electric current through a pipe under test, wherein the electric current comprises a plurality of harmonic components;

measuring a spectrum of the harmonic components of the electric current;

measuring a magnetic field produced outside said pipe as a result of passing said electric current through said pipe;

analyzing a spectrum of the harmonic components of said measured magnetic field; and evaluating ratios between identical spectral components of said electric current and said magnetic field to recognize pipe wall thickness irregularities based on frequency dependency of the magnetic field upon the electric current.

2. A test apparatus for noncontact and nondestructive recognition of irregularities in the wall thickness of ferromagnetic pipes, comprising:

a current source, for supplying an electric current for passing through the pipe under test, wherein the electric current comprises a plurality of harmonic components;

means for measuring a spectrum of the harmonic components of said electric current;

at least one magnetic field sensor, for measuring and storing a spectrum of the harmonic components of a magnetic field produced outside said pipe by passing said electric current;

means for comparing and analyzing the measured spectral data of the harmonic components of the electric current and the magnetic field.

\* \* \* \* \*